United States Patent [19]

Kerherve et al.

[11] Patent Number: 4,812,332
[45] Date of Patent: Mar. 14, 1989

[54] METHOD FOR FORMING A COATED SUBSTRATE

[76] Inventors: Jean-Pierre Kerherve, 28 bis, Chemin des Fonceaux Linas, 91310 Monthlery; Armel Queromes, Appr. 123-Residence du Foulon, 91120 Villebon Sur Yvette, both of France

[21] Appl. No.: 64,022

[22] Filed: Jul. 27, 1987

Related U.S. Application Data

[62] Division of Ser. No. 765,739, Aug. 14, 1985, Pat. No. 4,694,091.

[30] Foreign Application Priority Data

Aug. 22, 1984 [FR] France ............... 84 13069

[51] Int. Cl.$^4$ .................. B05D 5/06; B05D 5/12
[52] U.S. Cl. ..................... 427/168; 427/108; 427/126.2; 427/126.3; 427/165; 427/226; 427/314; 65/60.52
[58] Field of Search ............ 427/165, 168, 126.2, 427/126.3, 108, 314, 205, 226; 65/60.52

[56] References Cited

U.S. PATENT DOCUMENTS

| | | | |
|---|---|---|---|
| 3,677,814 | 7/1972 | Gillery | 117/211 |
| 3,792,059 | 2/1974 | Hechenbleikner | 556/104 |
| 4,036,866 | 7/1977 | Larkin | 556/104 |
| 4,182,783 | 1/1980 | Henery | 427/248 B |
| 4,254,046 | 3/1981 | Franz et al. | 260/429.7 |
| 4,325,988 | 4/1982 | Wagner | 427/160 |
| 4,533,571 | 8/1985 | Kramer et al. | 427/180 |

FOREIGN PATENT DOCUMENTS

| | | |
|---|---|---|
| 39256 | 11/1981 | European Pat. Off. . |
| 2542636 | 9/1984 | France . |

*Primary Examiner*—Janyce Bell
*Attorney, Agent, or Firm*—Pennie & Edmonds

[57] ABSTRACT

A method for preparing dibutyl tin difluoride which comprises reacting dibutyl tin chloride and ammonium fluoride to form dibutyl tin difluoride; dissolving the dibutyl tin difluoride in an appropriate solvent to form a solution; adding a refractory powder having a predetermined particle size to the solution to act as a recrystallization initiator; rapidly cooling the solution to recrystallize the dibutyl tin difluoride; washing the recrystallized dibutyl tin difluoride at least once with a suitable solvent; and recovering a final dibutyl tin difluoride product having spherical grains averaging 15–25 microns in size which are free of alkaline-earth and alkali impurities. The products produced by this process. A method for depositing tin oxide upon a substrate which comprises preparing a dibutyl tin difluoride powder by the method described above; providing a heated substrate; and depositing the dibutyl tin difluoride powder upon a desired surface portion of the heated substrate so as to pyrolyze the powder, thus coating the desired surface portion with tin oxide.

14 Claims, No Drawings

METHOD FOR FORMING A COATED SUBSTRATE

This is a division of application Ser. No. 765,739, filed Aug. 14, 1985, now U.S. Pat. No. 4,694,091.

TECHNICAL FIELD

This invention concerns the preparation of a dibutyl tin difluoride (DBTF) powder intended to be deposited on a substrate at high temperatures, so as to yield a tin oxide coating after pyrolysis.

BACKGROUND ART

Coatings of dibutyl tin difluoride (DBTF) powder on glass are frequently employed with a view to reinforcing their surface, staining it and provided such surfaces with specific optical and/or electrical characteristics, most notably, low emissivity. The use of powdered DBTF to obtain such a coating with low emissivity, is described in European Pat. No. 39 256.

DBTF is conventionally manufactured from dibutyl tin dichloride (DBTCl) and potassium fluoride in a water-alcohol medium, according to the reaction:

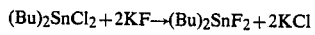
$$(Bu)_2SnCl_2 + 2KF \rightarrow (Bu)_2SnF_2 + 2KCl$$

However, the DBTF thus obtained contains potassium as an impurity. It is also known that DBTF can be synthesized from sodium fluoride or other alkaline or alkaline-earth fluorides, however the DBTF obtained by this process contains sodium and, in general, an alkali or an alkaline earth as impurities.

The alkaline earth or alkaline, such as sodium or potassium, when encountered in the pyrolyzed coating, captures any available free electric charges. This results in a reduction of the optical ane electrical characteristics of the coating in relation to those of a coating which is free of these impurities.

Furthermore, the DBTF powder is usually applied to a substrate to be coated, such as, e.g. a glass strip coming out of a float bath, by means of a nozzle of the type described in French patent application Nos. FR 83/4,124 and 83/4,125. The coating will be of a uniform quality if the powder flows well in the distributing and proportioning devices above the nozzle and in the nozzle itself, but prior art DBTF powders often tend to become agglomerated at these points. The alkaline-earth or alkaline impurities, particularly, sodium or otassium, which are present in the powder, render is hygroscopic, and this impairs its flowability due to the consequent agglomeration which occurs. The agglomeration, in turn, is detrimental to obtaining a homogeneous coating due to its obstruction of powder flow.

In order to remedy this flow problem, it is possible to eliminate these impurities by one or usually more additional operations, such as a purification step, but this is a lengthy and expensive procedure.

SUMMARY OF THE INVENTION

The invention relates to a method for preparing dibutyl tin difluoride which comprises reacting dibutyl tin chloride with ammonium difluoride to form dibutyl tin difluoride, dissolving the dibutyl tin difluoride in an appropriate solvent to form a solution, adding a refractory powder having a predetermine particle size to the solution in an amount sufficient to act as a recrystallization initiator, cooling the solution at a sufficient rate to recrystallize the dibutyl tin difluoride, washing the recrystalized dibutyl tin difluoride to remove any remaining dibutyl tin chloride or solvent, and recovering a dibutyl tin difluoride product having spherical grains averaging about 15-25 microns in size which are free of alkaline-earth and alkali impurities.

In this method, the dibutyl tin difluoride can be recrystallized at least once before adding the refractory powder. The rate of solution cooling comprises a temperature differential of at least about 45° C., and can be accomplished by spraying the solution into a proportionally larger quantity of cold alcohol.

The preferred refractory powder is silica having a particle size of between about 7 and 20 nanometers. Advantageously, the silica to added in an amount of about 0.5 to 5% by weight based on the weight of the dibutyl tin difluoride. Also, the washing step comprises contacting the dibutyl tin difluoride with at least one chlorinated or chlorofluorinated solvent or mixtures thereof.

A preferred method for preparing this impurity-free dibutyl tin difluoride comprises reacting dibutyl tin chloride an ammonium difluoride to form dibutyl tin difluoride, dissolving the dibutyl tin difluoride in alcohol, recrystallizing the dibutyl tin difluoride at least once, disolving the recrystallized dibutyl tin difluoride in alcohol to form a solution, adding silica having a particle size of between about 7 and 20 nanaometers to the solution in an amount of between about 0.5 and 5% by weight based on the weight of the dibutyl tin difluoride to act as a recrystallization initiaytor, cooling the solution by a temperature differential of between about 45° and 90° C. to recrystallize the dibutyl tin difluoride, washing the recrystallized dibutyl tin difluoride at least once to remove any remaining dibutyl tin chloride or alcohol, and recovering a dibutyl tin difluoride having spherical grains averaging 15-25 microns in size which are free of alkaline-earth and alkali impurities.

The invention also relates to the alkali-free and alkaline earth-free dibutyl tin difluoride products produced by the previously described processes.

Another aspect of the invention relates to a method for depositing tin oxide upon a substrate which comprises preparing a dibutyl tin difluoride powder by one of the methods described above, providing a heated substrate, and depositing the dibutyl tin difluoride powder upon a desired surface portion of the heated substrate so as to pyrolyze the powder, thus coating the desired surface portion with tin oxide. In these methods, the substrate is at least one of glass, a metal or a ceramic or other refractory material. Preferably, the substrate is float glass, and the powder is deposited onto the desired surface portion by spraying it through a nozzle.

An alternate embodiment of these methods for depositing tin oxide includes providing a heated substrate and depositing an alkali-free and/or alkaline earth free dibutyl tin difluoride powder product as described above upon a desired surface portion of the heated substrate so as to pyrolyze the powder, thus coating the desired surface portion with tin oxide.

DETAILED DESCRIPTION OF THE PREFERRED EMBODIMENTS

The present invention provides a method for preparing a dibytl tin difluoride compound ("DBTF") which does not contain disturbing alkaline-earth or alkaline impurities, particularly, sodium or potassium, thus producing coatings which are, on the one hand, more homogeneous and uniform and, on the other, free of impurities which are likely to interfere with the optical and electrical characteristics of the coating.

The novel process of the invention also provides a DBTF powder with grains having a shape and size enabling them to be easily and regularly carried through the devices used for distributing the coating onto the surface of a substrate.

Advantageously, dibutyl tin chloride and an ammonium difluoride are reacted to form a dibutyl tin difluoride precipitate. Dibutyl tin dichloride (DBTCl) is solubilized in an alcohol, preferably methanol, in a first reaction vessel. In a second such vessel, ammonium difluoride (NH$_4$F, HF) is dissolved in a solvent which is preferably water. The contents of one reaction vessel are poured into the other and, on contact of the two solutions, a dibutyl tin difluoride precipitate is formed. The mixture is stirred to enhance the contact between the two solutions and to maximize the yield of precipitate. The resulting precipitate is recovered, drained, washed with water, washed with a solvent such as acetone to eliminate any remaining water and dried.

To purify the DBTF obtained in the prior reaction, the precipitate is redissolved in an appropriate solvent, e.g., an alcohol, preferably methanol; heated, if necessary, to dissolve all DBTF and to form a solution; and the dissolved DBTF is then recrystallized. This purification step may be repeated several times, if desired.

During the purification step, (or during the final purification step if more than one is utilized), a finely divided powder of predetermined particle size is added, preferably under agitation. Generally, any refractory powder can be used. A finely divided silica marketed under the name of Aerosil ® 972 is preferred. The powder utilized, in general, ranges between about 7 and 20 nanometers, and preferably averages about 15 nanometers in size, i.e., on the order of 1/1000 of the size desired for the DBTF powder. The refractory powder is added to the solution to act as a recrystallization initiator, preferably in proportions of from 0.5% to 5% by weight, based upon the weight of the DBTF.

To enhance the crystallization of the DBTF, a sudden cooling of a differential temperature of at least 45° C., and generally ranging between about 45° and 90° C. is carried out. Such rapid cooling can be obtained by pouring the DBTF/refractory powder solution into a cold solvent reserve.

Thus, for example, when the DBTF is in a heated methanol solution, at a temperaure of approximately 70° C., the silica is added and the hot DBTF solution then is poured into a large quantity of cold alcohol, preferably, methanol at a temperature of about −20° C. Advantageously, for the cooling rate to be sufficient at the end of pouring the hot solution, the quantity of cold alcohol should be approximately equal to or greater than half of the quantity of hot solution. Advantageously, in order to obtain this sudden cooling, while limiting the quantity of cold solvent necessary, the cold solvent can be continuously cooled during pouring. Using those proportions, a solvent cooled initially to −20° C. will rise in temperature to +25° C. after the pouring of the hot DBTF solution is completed, so that differential cooling is from approximately 45° C. to 90° C.

Alternatively, to obtain superior cooling, as well as increased consistency in the size of the grains, the cooling may be performed by spraying the hot DBTF solution into cold alcohol. Preferably, to obtain an identical cooling for all of the hot DBTF/silica solution, this cooling operation should take place in an intermediate tank, with small quantities of cold alcohol being taken successively from the tank containing all of the alcohol intended for the entire cooling operation, and small quantities of hot DBTF solution being successively introduced by pouring or spraying the solution into the small quantites of alcohol.

The addition of finely divided powder grains of a size on the order of 15 nanometers, such as for example, the Aerosil ® material mentioned previously, may then serve as a crystallization initiator, and the rapid cooling causes the DBTF to precipitate in fine, regular grains.

The purified precipitate then is drained, washed, dried and screened. The screening stage advantageously includes at least one washing step with a chlorinated solvent such as methylene chloride, a chlorofluorinated solvent such as trichlorotrifluoroethane, or with mixtures of such solvents. The dibutyl tin difluoride precipitate, which comprises spherical grains averaging 15–25 microns in size and are free of alkaline-earth and alkali impurities, is then recovered from the solution.

The washing step removes the alcohol, e.g. methanol left on the crystals, and solubilizes and eliminates the remaining traces of dibutyl tin dichloride. It is necessary to remove dibutyl tin dichloride because it is hygroscopic and thus prejudicial to good flowability. The removal of alcohol also favors drying of the powder.

The washing step can advantageously be carried out using a technique known in the art as "clarifying." This technique involves repeated successive extractions from a suspension of the DBTF particles by means of a process such as centrifugation, utilizing a minimal amount of solvent. This washing ste can also be performed during other stages of synthesis, but may reduce the yield of DBTF. Thus it is preferred to carry out this washing step after obtaining the desired size of DBTF powder.

The spherical grains of DBTF form a powder that flows well and will not agglomerate. This good flowability is due to the shape and size of the trains, as well as due to the fact that these grains do not contain impurities of potassium, sodium, alkalis, or alkaline earths. The fine refractory powder, such as Aerosil ®, introduced during a purification step also coats the grains, so as to promote their sliding over each other. Thus, the particles are relatively unaffected by moisture, and have good flowability.

The dibutyl tin difluoride precipitate obtained by the process described above may be used to coat a substrate such as ceramic, metal or preferably, glass. The coating may be deposited upon the surface of the substrate by preparing the dibutyl tin difluoride powder as outlined above, pyrolyzing the powder so as to form tin oxide and depositing the resultant tin oxide onto the surface of the substrate.

EXAMPLE

The following example demonstrates the applicant's improved method for the synthesis of DBTF which is free of alkali and alkali earth impurities. This example is set forth for the purpose of illustration only and is not to be construed as limiting the scope of the invention in any manner.

The following are reacted:
156 kg. of dibutyl tin chloride,
256 kg. of methanol,
44 kg. of ammonium difluoride, and 240 kg of water From this reaction, 125 kg of raw DBTF (dry) was recovered as a precipitate.

This 125 kg. of DBTF was dissolved in 2,000 kg of methanol by heating to about 70° C. Next, 1.25 kg. of Aerosil ® was added and the solution was poured in approximately 5 minutes into 1,000 kg. of methanol at −20° C. After draining, washing, drying and screening to 60 microns, 100 kg. of DBTF powder, ready for use, was collected.

DBTF produced by the improved method of the present invention can preferably be used to coat glass substrates, preferably, windows, but such coatings can also be deposited on substrates of others kinds, e.g., metals, ceramics, etc.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

We claim:

1. A method for depositing tin oxide upon a substrate which comprises:
    preparing a dibutyl tin difluoride powder by a method comprising
        reacting dibutyl tin chloride and an ammonium difluoride to form dibutyl tin difluoride;
        forming a solution of said dibytl tin difluoride,
        adding a refractory powder to said solution to act as a recrystallization initiator,
        cooling the solution to recrystallize the dibutyl tin difluoride, and
        recovering a dibutyl tin difluoride product having spherical grains and being free of alkaline earth and alkali impurities;
    providing a heated substrate; and
    depositing the dibutyl tin difluoride powder upon a surface portion of said heated substrate so as to pyrolyze the powder, thus coating the desired surface portion with tin oxide.

2. The method of claim 1 wherein the substrate is at least one of glass, a metal or a ceramic or other refractory material.

3. The method of claim 2 wherein the substrate is float glass.

4. The method of claim 2 wherein the powder is deposited onto the desired surface portion of the substrate by spraying it through a nozzle.

5. A method for depositing tin oxide upon a substrate which comprises:
    preparing a dibutyl tin difluoride powder by a method comprising
        reacting dibutyl tin chloride and ammonium difluoride to form dibutyl tin difluoride,
        dissolving the dibutyl tin difluoride in alcohol, recrystallizing the dibutyl tin difluoride at least once,
        dissolving the recrystallized dibutyl tin difluoride in alcohol to form a solution,
        adding silica having a particle size of between 7 and 20 nanometers to the solution in an amount of between about 0.5 and 5% by weight based upon the weight of the dibutyl tin difluoride to act as a recrystallization initiator,
        cooling the solution by a temperature differential of between about 45° and 95° to recrystallize the dibutyl tin difluoride,
        washing the recrystallized dibutyl tin difluoride at least once to remove any remaining dibutyl tin chloride or alcohol, and
        recovering a dibutyl tin difluoride having spherical grains averaging about 15–25 microns in size which are free of alkaline-earth and alkali impurities;
    providing a heated substrate; and
    depositing the dibutyl tin difluoride powder upon a desired surface portion of the heated substrate so as to pyrolyze the powder, thus coating the desired surface portion with tin oxide.

6. The method of claim 5 wherein the substrate is at least one of glass, a metal or a ceramic or other refractory material.

7. The method of claim 5 wherein the substrate is float glass.

8. The method of claim 5 wherein the powder is deposited onto the desired surface portion of the substrate by spraying it through a nozzle.

9. The method of claim 1 wherein said solution is rapidly cooled by spraying into a proportionally larger quantity of cold alcohol.

10. The method of claim 1 which further comprises agitating said solution of dibutyl tin difluoride during the addition thereto of said refractory powder.

11. The method of claim 5 wherein said solution is rapidly cooled by spraying into a proportionally larger quantity of cold alcohol.

12. The method of claim 15 wherein the washing step comprises contacting the dibutyl tin difluoride with at least one chlorinated or chlorofluorinated solvent or mixtures thereof.

13. The method of claim 5 which further comprises agitating said solution of dibutyl tin difluoride during the addition thereto of said silica.

14. In a method for depositing tin oxide upon a substrate by decomposing a dibutyl tin difluoride powder upon a desired surface portion of a heated substrate the improvement which comprises utilizing a refractory coated alkali-free and alkaline-earth free dibutyl tin difluoride powder having improved flowability so as to produce a uniform layer of tin oxide haing improved optical and electrical characteristics upon the desired surface portion of said substrate.

* * * * *